(12) United States Patent
Cooke et al.

(10) Patent No.: US 9,207,209 B2
(45) Date of Patent: Dec. 8, 2015

(54) METHOD AND APPARATUS FOR DETECTING SMOKE IN AN ION CHAMBER

(71) Applicant: Microchip Technology Incorporated, Chandler, AZ (US)

(72) Inventors: Benjamin T. Cooke, Denver, CO (US); Joseph Julicher, Maricopa, AZ (US); Keith Edwin Curtis, Gilbert, AZ (US)

(73) Assignee: MICROCHIP TECHNOLOGY INCORPORATED, Chandler, AZ (US)

( * ) Notice: Subject to any disclaimer, the term of this patent is extended or adjusted under 35 U.S.C. 154(b) by 430 days.

(21) Appl. No.: 13/667,165

(22) Filed: Nov. 2, 2012

(65) Prior Publication Data

US 2013/0154659 A1    Jun. 20, 2013

Related U.S. Application Data

(63) Continuation-in-part of application No. 13/633,686, filed on Oct. 2, 2012.

(60) Provisional application No. 61/570,436, filed on Dec. 14, 2011.

(51) Int. Cl.
   *G01N 27/66* (2006.01)
   *G08B 17/11* (2006.01)
   *H03M 3/00* (2006.01)
   *G08B 29/18* (2006.01)

(52) U.S. Cl.
   CPC ............... *G01N 27/66* (2013.01); *G08B 17/11* (2013.01); *H03M 3/30* (2013.01); *G08B 29/181* (2013.01)

(58) Field of Classification Search
   None
   See application file for complete search history.

(56) References Cited

U.S. PATENT DOCUMENTS

| | | | |
|---|---|---|---|
| 3,295,121 A | 12/1966 | Scheel | 340/629 |
| 3,832,678 A | 8/1974 | Gysell et al. | 340/587 |
| 4,213,047 A | 7/1980 | Mccord | 250/381 |
| 4,222,045 A | 9/1980 | Cholin | 340/628 |
| 4,260,984 A * | 4/1981 | Honma | 340/630 |
| 4,266,220 A | 5/1981 | Malinowski | 340/360 |
| 4,401,978 A | 8/1983 | Solomon | 340/628 |

(Continued)

FOREIGN PATENT DOCUMENTS

| | | | |
|---|---|---|---|
| CN | 1087739 A | 6/1994 | G08B 17/11 |
| CN | 101261225 A | 9/2008 | G01N 21/53 |

(Continued)

OTHER PUBLICATIONS

Yair, R., "Charge Sampling Method for Low Current Measurement," Review of Scientific Instruments, vol. 45, No. 3, 6 pages, Mar. 1974.

(Continued)

*Primary Examiner* — Melissa Koval
*Assistant Examiner* — Courtney McDonnough
(74) *Attorney, Agent, or Firm* — Slayden Grubert Beard PLLC

(57) ABSTRACT

A smoke detection sensor ion chamber has a leakage current that is dependent upon the permittivity of the ionized gas (air) in the chamber. Smoke from typical fires is mainly composed of unburned carbon that has diffused in the surrounding air and rises with the heat of the fire. The permittivity of the carbon particles is about 10 to 15 times the permittivity of clean air. The addition of the carbon particles into the air in the ion chamber changes the permittivity thereof that is large enough to detect by measuring a change in the leakage current of the ion chamber.

32 Claims, 5 Drawing Sheets

(56) References Cited

U.S. PATENT DOCUMENTS

| | | | |
|---|---|---|---|
| 4,538,137 A * | 8/1985 | Kimura | 340/512 |
| 4,652,866 A | 3/1987 | Siegmann et al. | 340/628 |
| 5,173,683 A * | 12/1992 | Brighenti et al. | 340/505 |
| 5,243,330 A | 9/1993 | Thuillard | 340/629 |
| 5,422,807 A | 6/1995 | Mitra et al. | 700/79 |
| 5,633,591 A | 5/1997 | Childress et al. | 324/399 |
| 5,705,988 A | 1/1998 | Mcmaster | 340/628 |
| 5,966,078 A | 10/1999 | Tanguay | 340/636.1 |
| 6,257,049 B1 | 7/2001 | Greybush | 73/29.01 |
| 6,433,712 B1 | 8/2002 | Ohnhaeuser et al. | 341/118 |
| 6,661,346 B1 | 12/2003 | Wood et al. | 340/601 |
| 6,981,090 B1 | 12/2005 | Kutz et al. | 710/317 |
| 7,288,946 B2 | 10/2007 | Hargreaves et al. | 324/678 |
| 7,307,485 B1 | 12/2007 | Snyder et al. | 331/150 |
| 7,382,140 B2 | 6/2008 | Obrecht | 324/678 |
| 7,460,441 B2 | 12/2008 | Bartling | 368/118 |
| 7,764,213 B2 | 7/2010 | Bartling et al. | 341/152 |
| 7,834,773 B2 | 11/2010 | Kato | 340/630 |
| 8,031,094 B2 | 10/2011 | Hotelling et al. | 341/143 |
| 8,487,655 B1 | 7/2013 | Kutz et al. | 326/86 |
| 8,547,135 B1 | 10/2013 | Yarlagadda et al. | 326/38 |
| 8,847,802 B2 | 9/2014 | Lundstrum et al. | 341/141 |
| 8,884,771 B2 | 11/2014 | Cooke et al. | 340/628 |
| 8,981,754 B1 | 3/2015 | Rohilla et al. | 323/312 |
| 9,035,243 B2 | 5/2015 | Lenkeit et al. | 250/287 |
| 2002/0078744 A1 | 6/2002 | Gehman et al. | 73/204.11 |
| 2002/0101345 A1 | 8/2002 | Pattok et al. | 340/516 |
| 2002/0153923 A1 | 10/2002 | Piasecki et al. | 326/57 |
| 2003/0058114 A1 | 3/2003 | Miller et al. | 340/577 |
| 2004/0257235 A1* | 12/2004 | Right et al. | 340/628 |
| 2005/0030172 A1 | 2/2005 | Right et al. | 340/521 |
| 2007/0075710 A1 | 4/2007 | Hargreaves et al. | 324/658 |
| 2008/0012715 A1 | 1/2008 | Montgomery | 340/579 |
| 2008/0079148 A1 | 4/2008 | Leung et al. | 257/734 |
| 2008/0111714 A1 | 5/2008 | Kremin | 341/33 |
| 2008/0272826 A1 | 11/2008 | Smit et al. | 327/509 |
| 2008/0312857 A1 | 12/2008 | Sequine | 702/65 |
| 2009/0230305 A1 | 9/2009 | Burke et al. | 250/336.1 |
| 2009/0256817 A1 | 10/2009 | Perlin et al. | 345/174 |
| 2010/0059295 A1 | 3/2010 | Hotelling et al. | 178/18.06 |
| 2010/0060593 A1 | 3/2010 | Krah | 345/173 |
| 2010/0097015 A1 | 4/2010 | Knoedgen et al. | 318/135 |
| 2010/0102832 A1 | 4/2010 | Bartling et al. | 324/679 |
| 2010/0181180 A1 | 7/2010 | Peter | 200/5 R |
| 2010/0231241 A1 | 9/2010 | Mueck et al. | 324/686 |
| 2010/0283760 A1 | 11/2010 | Leung et al. | 345/174 |
| 2010/0287571 A1 | 11/2010 | Mohammed et al. | 719/328 |
| 2010/0295555 A1 | 11/2010 | Emanuel et al. | 324/601 |
| 2011/0007028 A1 | 1/2011 | Curtis et al. | 345/174 |
| 2011/0234417 A1 | 9/2011 | Aleman et al. | 340/660 |
| 2011/0267287 A1 | 11/2011 | Bartling et al. | 345/173 |
| 2011/0267309 A1 | 11/2011 | Hanauer et al. | 345/174 |
| 2012/0005693 A1 | 1/2012 | Mohammed et al. | 719/328 |
| 2012/0098686 A1 | 4/2012 | Wang | 341/118 |
| 2012/0112728 A1 | 5/2012 | Bodo et al. | 323/311 |
| 2013/0088246 A1 | 4/2013 | Lundstrum et al. | 324/686 |
| 2013/0090873 A1 | 4/2013 | Lundstrum et al. | 702/64 |
| 2013/0126715 A1 | 5/2013 | Flaherty | 250/214 R |
| 2013/0298100 A1 | 11/2013 | Hastings et al. | 716/126 |
| 2013/0322439 A1 | 12/2013 | Verhollen et al. | 370/389 |

FOREIGN PATENT DOCUMENTS

| | | | | |
|---|---|---|---|---|
| CN | 102257543 A | | 11/2011 | G08B 11/00 |
| DE | 10357371 A1 | | 7/2005 | G08B 17/00 |
| DE | 102009030495 A1 | | 1/2011 | G01B 7/00 |
| EP | 1719947 A1 | | 11/2006 | F23N 5/12 |
| FR | 2473201 A1 | | 7/1981 | G08B 17/11 |
| GB | 1313877 A | * | 11/1970 | G01N 21/27 |
| GB | 1598821 A | | 9/1981 | G08B 17/11 |
| GB | 2117560 A | | 10/1983 | G01N 27/64 |
| GB | 2156126 A | | 10/1985 | G08B 17/00 |
| WO | 2006/138205 A1 | | 12/2006 | H03M 1/06 |

OTHER PUBLICATIONS

Margarita, Andrey, "Application Note AN2245: Smart Smoke Detector," Cypress Semiconductor Corporation, XP055054690, URL: http://www.psocdeveloper.com/uploads/tx_piapappnote/an2245_01.pdf, 12 pages, Feb. 22, 2005.

Perme, Thomas, "AN1101: Introduction to Capacitive Sensing," Microchip Technology, Inc., XP002693941, URL: http://ww1.microchip.com/downloads/en/AppNotes/01101A.pdf, 10 pages, Jun. 25, 2007.

Bohn, Bruce, "AN1250: Microchip CTMU for Capacitive Touch Applications," Microchip Technology, Inc., XP055007432, URL: http://www.microchip.com/stellent/idcplg?IdcService=SS_GET_PAGE&nodeID=1824&appnote=en539441, 22 page, Feb. 3, 2009.

Perme, Thomas et al., AN1298: Capacitive Touch Using Only an ADC ("CVD"), Microchip Technology, Inc., XP055007357, URL: http://www.microchip.com/stellent/idcplg?IdcService=SS_GET_PAGE&nodeId=1824&appnote=en545264, 4 pages, Oct. 7, 2009.

Davison, Burke, "AN1334: Techniques for Robust Touch Sensing Design," Microchip Technology, Inc., XP055047201, URL: http://www.microchip.com/downloads/en/AppNotes/01334A.pdf, 28 pages, Aug. 6, 2010.

Yedamale, Padmaraja et al., "AN1375: See What You Can Do with the CTMU," Microchip Technology, Inc., XP055047211, URL: http://www.microchip.com/downloads/en/AppNotes/CTMU%2001375a.pdf, 12 pages, May 11, 2011.

Anonymous, "Delta-Sigma Modulation," Wikipedia, URL: http://en.wikipedia.org/w/index.php?title=Special:Book&bookcmd=download&collection_id=fa136df1282a073a&writer=r1&return_to=Delta-sigma modulation, 14 pages, 2012.

International Search Report and Written Opinion, Application No. PCT/US2012/058682, 12 pages, Dec. 17, 2012.

International Search Report and Written Opinion, Application No. PCT/US2012/058691, 13 pages, Dec. 19, 2012.

International Search Report and Written Opinion, Application No. PCT/US2012/058832, 11 pages, Jan. 22, 2013.

International Search Report and Written Opinion, Application No. PCT/US2012/058837, 14 pages, Feb. 18, 2013.

International Search Report and Written Opinion, Application No. PCT/US2012/058716, 10 pages, Mar. 15, 2013.

International Search Report and Written Opinion, Application No. PCT/US2012/069086, 10 pages, Apr. 5, 2013.

International Search Report and Written Opinion, Application No. PCT/US2012/069094, 12 pages, Apr. 5, 2013.

International Search Report and Written Opinion, Application No. PCT/US2012/058688, 11 pages, Apr. 5, 2013.

International Search Report and Written Opinion, Application No. PCT/US2012/069076, 11 pages, Apr. 10, 2013.

International Search Report and Written Opinion, Application No. PCT/US2012/070466, 13 pages, Apr. 24, 2013.

International Search Report and Written Opinion, Application No. PCT/US2013/052956, 12 pages, Jan. 28, 2014.

U.S. Advisory Action, U.S. Appl. No. 13/709,399, 3 pages, Sep. 8, 2015.

Cuilan, Tan, Research & Design of Wireless Smoke Detection System, Engineering Science and technology II, China Master's Theses (Chinese language), 1 page. (English abstract), Sep. 15, 2009.

Chinese Office Action, Application No. 201280068100.7, 5 pages, Oct. 9, 2015.

* cited by examiner

METHOD AND APPARATUS FOR DETECTING SMOKE IN AN ION CHAMBER

RELATED PATENT APPLICATION

This application claims priority to commonly owned U.S. Provisional Patent Application Ser. No. 61/570,436; filed Dec. 14, 2011; entitled "Method and Apparatus for Detecting Smoke," by Benjamin T. Cooke, Joseph Julicher and Keith Edwin Curtis; and is a Continuation-In-Part of U.S. patent application Ser. No. 13/633,686; filed Oct. 2, 2012; entitled "Differential Current Measurements to Determine Ion Current in the Presence of Leakage Current," by Joseph Julicher, Keith Curtis and Paul N. Katz; both of which are hereby incorporated by reference herein for all purposes.

TECHNICAL FIELD

The present disclosure relates to smoke detection devices, and more particularly, to a smoke detection device that uses a delta-sigma analog-to-digital converter for determining when smoke is present in ion chamber.

BACKGROUND

A smoke detector generally uses an ionization chamber containing a radioactive ion source that is coupled to a high input impedance operational amplifier. FIG. 1 shows a typical ionization chamber used in a smoke detector to produce a very small current (nA) that is reduced in the presence of smoke particles. Operational amplifiers are used to convert this current to a voltage that is then measured to determine the presence of smoke. Elevated temperatures cause increased leakage currents on the inputs of the operational amplifier in the smoke detector. This affects overall performance of the ionization chamber smoke detection function. Thus, such increases in leakage currents can pose a variety of problems such as inaccuracy, etc. which may require further compensation circuits when designing a smoke detector and therefore may increase the cost of the device.

Furthermore, the impedance of the ion chamber is extremely high, and any leakage currents, e.g., printed circuit board leakage current, masks the ion chamber current. Smoke detection ion chambers therefore require a complex manufacturing process where pins of the sensing integrated circuit operational amplifier are bent and directly welded in mid-air to the ion chamber. As mentioned above, special low leakage circuits are required to detect the small current change through the ion chamber caused by the presence of smoke therein.

SUMMARY

Therefore, a need exists for a way to detect smoke in an ion chamber of a smoke detector that does not require sensitive and expensive components nor complex manufacturing processes.

According to an embodiment, a method for detecting smoke may comprise the steps of: determining a voltage on a conductive screen with a delta-sigma analog-to-digital converter, wherein the conductive screen may be located between a first ion chamber and a second ion chamber, wherein the first ion chamber may be open to smoke ingress and the second ion chamber may be closed to smoke ingress; and detecting a presence of smoke when the voltage on the conductive screen changes by a certain amount.

According to a further embodiment of the method, may comprise the steps of: applying a first voltage potential to the first and second ion chambers at a first polarity; determining a first voltage on the conductive screen caused by the first voltage potential at the first polarity; applying a second voltage potential to the first and second ion chambers at a second polarity; determining a second voltage on the conductive screen caused by the second voltage potential at the second polarity; determining a voltage difference between the first and the second voltages; and detecting the presence of smoke when the voltage difference changes by a certain amount. According to a further embodiment of the method, the voltage on the conductive screen changes by the certain amount within a certain time.

According to a further embodiment of the method, the step of determining the voltage on the conductive screen may comprise the steps of: comparing the voltage on the conductive screen to a reference voltage from a voltage reference with a voltage comparator; charging a capacitance coupled between the conductive screen and the voltage reference when the voltage on the conductive screen may be less than the reference voltage; discharging the capacitance coupled between the conductive screen and the voltage reference when the voltage on the conductive screen may be greater than the reference voltage; counting the number of times the capacitance may be charged during a sample time; and comparing the number of times the capacitance may be charged during the sample time to determine whether a count number of any one or more of the subsequent sample times has changed by a certain number of counts.

According to a further embodiment of the method, the step of determining the voltage on the conductive screen may comprise the steps of: comparing the voltage on the conductive screen to a reference voltage from a voltage reference with a voltage comparator; charging a capacitance coupled between the conductive screen and the voltage reference when the voltage on the conductive screen may be less than the reference voltage; discharging the capacitance coupled between the conductive screen and the voltage reference when the voltage on the conductive screen may be greater than the reference voltage; counting the number of times the capacitance may be discharged during a sample time; and comparing the number of times the capacitance may be discharged during the sample time to determine whether a count number of any one or more of the subsequent sample times has changed by a certain number of counts.

According to a further embodiment of the method, may comprise the step of compensating for temperature change with temperature information from a temperature sensor. According to a further embodiment of the method, may comprise the step of compensating for relative humidity change with relative humidity information from a relative humidity sensor. According to a further embodiment of the method, may comprise the step of compensating for voltage change with voltage information from a voltage sensor.

According to a further embodiment of the method, may comprise the steps of: counting clock pulses from a clock generator in a first counter when the capacitor may be being charged; counting clock pulses from the clock generator in a second counter during the sample time; and comparing a first count value from the first counter of the number of clock pulses counted therein with a second count value from the second counter of the number of clock pulses counted therein; wherein if the first count value may be less then the second count value by a certain amount then generating a smoke alarm.

According to a further embodiment of the method, may comprise the steps of: subtracting the first count value from the second count value to produce a difference value; and dividing the first count value by the second count value to produce a proportional count value.

According to another embodiment, an apparatus for detecting smoke may comprise: an ionization chamber having a radiation source and comprising first and second chambers with a conductive screen therebetween, wherein the first chamber may be open to smoke ingress and the second chamber may be closed to smoke ingress; a voltage comparator having a first input coupled to the conductive screen and a second input coupled to a voltage reference; a capacitor coupled between the first and second inputs of the voltage comparator; a flip-flop having a D-input coupled to an output of the voltage comparator and a clock input coupled to a clock generator, wherein each time a clock signal may be received from the clock generator a logic value at the D-input may be transferred to a Q-output of the flip-flop; a feedback resistor coupled between the Q-output of the flip-flop and the first input of the voltage comparator for charging and discharging the capacitor; wherein when a voltage on the first input of the voltage comparator may be greater than a voltage from the voltage reference the output of the voltage comparator may be at a logic low and the capacitor may be discharged, and when the voltage on the first input of the voltage comparator may be less than the voltage from the voltage reference the output of the voltage comparator may be at a logic high and the capacitor may be charged; a first counter for counting a first number of clock pulses from the clock generator when the Q-output of the flip-flop may be at a logic high during a certain time period; and a second counter for counting a second number of clock pulses from the clock generator during a certain time period; wherein when the first number changes a certain amount within the certain time period a presence of smoke may be detected within the first chamber.

According to a further embodiment, circuits may be provided for alternately coupling the ionization chamber to voltage potentials at first or second polarities, wherein the second polarity may be opposite the first polarity. According to a further embodiment, the circuits for alternately coupling comprises voltage multiplexers. According to a further embodiment, the ionization chamber may be coupled to a microcontroller having a digital processor and memory, and the microcontroller performs all of the aforementioned functions for detecting the presence of smoke. According to a further embodiment, an alarm circuit may be coupled to the digital processor.

According to a further embodiment, a temperature sensor may be coupled to the digital processor and a temperature compensation look-up table stored in the memory coupled to the digital processor and used to compensate temperature induced changes of the capacitance of the ionization chamber. According to a further embodiment, a humidity sensor may be coupled to the digital processor and a humidity compensation look-up table stored in the memory coupled to the digital processor and used to compensate humidity induced changes of the capacitance of the ionization chamber. According to a further embodiment, a voltage sensor may be coupled to the digital processor and a voltage compensation look-up table stored in the memory coupled to the digital processor and used to compensate voltage induced changes of the capacitance of the ionization chamber.

According to a further embodiment, an audible alert may be actuated by the presence of smoke in the ionization chamber. According to a further embodiment, a visual alert may be actuated by the presence of smoke in the ionization chamber.

According to a further embodiment, a microcontroller having a low power sleep mode may be provided, wherein the digital processor and memory of the microcontroller go into the low power sleep mode during counting by the first and second counters. According to a further embodiment, the second counter may be a sleep wake-up timer for the digital processor and memory of the microcontroller.

BRIEF DESCRIPTION OF THE DRAWINGS

A more complete understanding of the present disclosure may be acquired by referring to the following description taken in conjunction with the accompanying drawings wherein.

Figure 1:
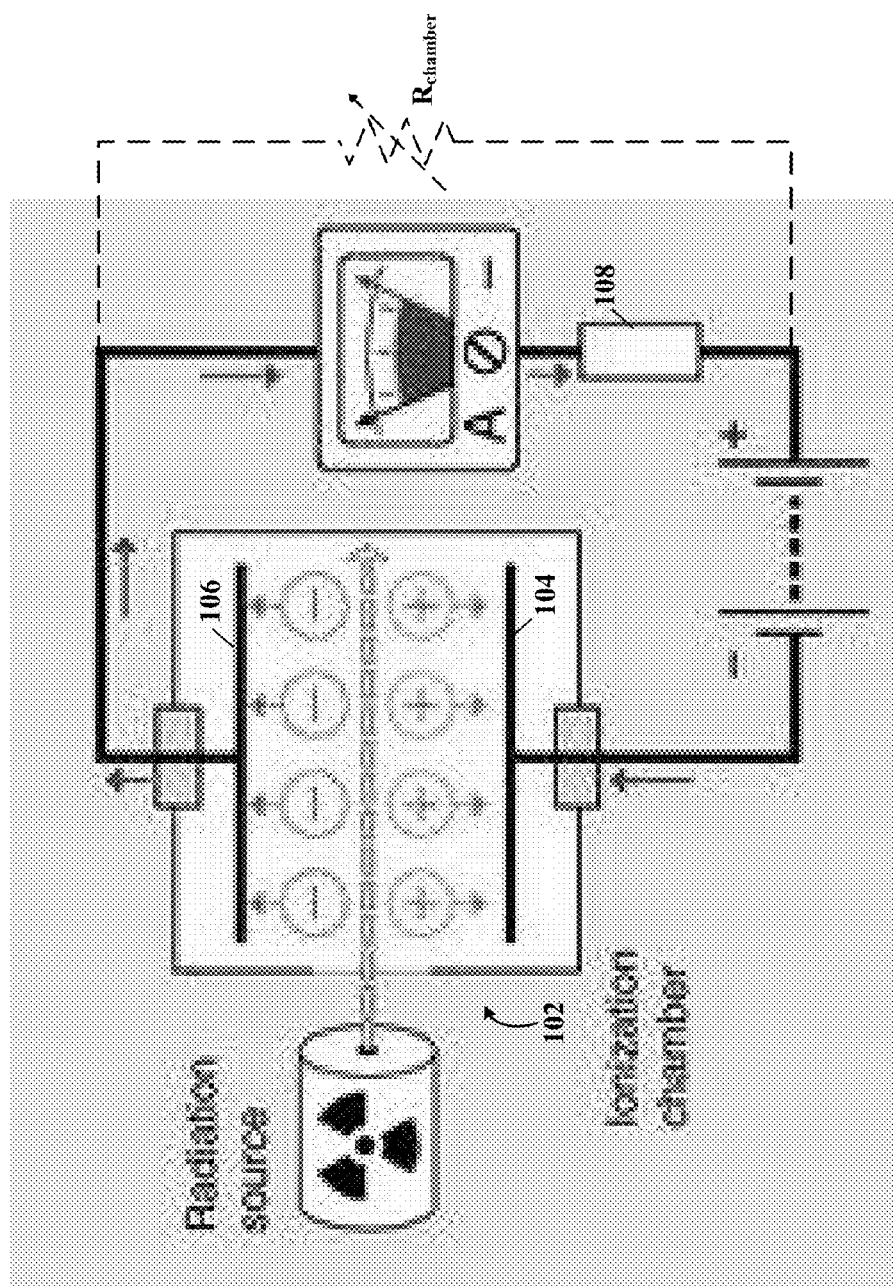
FIG. 1 illustrates a schematic diagram of an ion chamber having a radiation source and used as a smoke detection sensor.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

A radioactive source in an ion chamber causes some of the gas (e.g., air) molecules in the chamber to ionize. The results is a higher than normal permittivity of the gas due to the higher than normal number of electrically polarized (ionized) gas molecules. Therefore, when a voltage is placed across two of the ion chamber electrodes (see FIG. 1) a small current will flow through the this ionized gas. When smoke enters the ion chamber, the smoke reacts with the ionized gas molecules thereby changing the permittivity, $\epsilon$, thereof, and reduces the number of ionized gas molecules. This results in a lower leakage current through the ion chamber. The ion chamber current leakage will vary with temperature, relative humidity and voltage variations. But these variations are very slow to change. However, smoke causes a sudden change in the ion chamber leakage current (reduces the leakage current). Therefore according to various embodiments, a delta-sigma converter may be used to detect changes in this leakage current.

By using a sigma delta analog-to-digital converter (ADC), the accuracy of analog-to-digital conversion of the leakage current through the ion chamber can be increased to a level sufficient to resolve a leakage current change generated by the presence of smoke. By using a differential technique according to various embodiments, the parasitic leakage can be subtracted from the "smoke" signal and the "smoke" signal amplitude increased by a factor of 2. The parasitic leakage currents can be subtracted from the signals present on an ion chamber by using differential techniques and a high resolution sigma delta ADC. This makes it possible to measure the presence of smoke without additional external components beyond the ion chamber. Eliminating the external circuitry and special manufacturing processes can save a smoke detector vendor a considerable amount of money.

Temperature and battery voltage variations can make significant differences in the permittivity of the gas (air) with corresponding variations in the leak current of a first ion chamber. By providing a second ion chamber that is sealed from smoke entering, a comparison of the measured leakage current values of each of the first and second ion chambers can be used to compensate for these variations and provide a sensitive way of detecting smoke particles. For example, subtracting the first ion chamber leakage current value from the second ion chamber leakage current value and then dividing by the second ion chamber leakage current value, removes the temperature and battery voltage effects, leaving a resultant value with is primarily affected by the presence of smoke in the first ion chamber.

Temperature, relative humidity (RH) and/or battery voltage sensors may be incorporated into a smoke detection system for determining the compensation necessary for the leakage current measurements of the ion chamber used for smoke detection. Permittivity variations due to temperature, RH and/or voltage changes generally are over a longer time period than a sudden change in the amount of contaminates (carbon particles, etc.) in the air of the ion chamber used for smoke detection. Another less sensitive way to ignore permittivity variations due to temperature, RH and/or voltage changes, would be to use an envelope detection or averaging process to ignore the slow drift of ion chamber leakage current due to voltage and/or temperature changes but recognize a more abrupt (rapid) change of the permittivity of air due to carbon particles suddenly showing up in the ion chamber. A mixed signal (analog and digital functions) microcontroller may used for leakage current measurements using a delta sigma ADC, doing the calculations necessary to determine whether smoke is present in the ion chamber, and compensate for and/or average out permittivity changes due to temperature, RH and/or battery voltage changes.

Referring now to the drawing, the details of specific example embodiments are schematically illustrated. Like elements in the drawings will be represented by like numbers, and similar elements will be represented by like numbers with a different lower case letter suffix.

Referring to FIG. 1, depicted is a schematic diagram of an ion chamber having a radiation source and used as a smoke detection sensor. The ion chamber 102 may be characterized as two electrodes some ionized gas molecules therebetween, e.g., electrodes 104 and 106. The gas molecules are ionized by the radiation source and when a voltage is applied between the two electrodes 104 and 106 a current will flow through the ionized gas characterized as a very high resistance, $R_{chamber}$, and a resistor 108 connected in series with the electrodes 104 and 106. This current produces a voltage across the resistor 108. By measuring the voltage across the resistor 108, the permittivity, $\epsilon$, of the gas may be determined. Smoke in the ion chamber will cause an abrupt change in the permittivity, $\epsilon$, causing an abrupt change in the current flow and voltage across the resistor 108. This voltage is measured by a very high impedance operational amplifier (not shown) which requires complex circuitry and manufacturing processes.

Figure 1A:
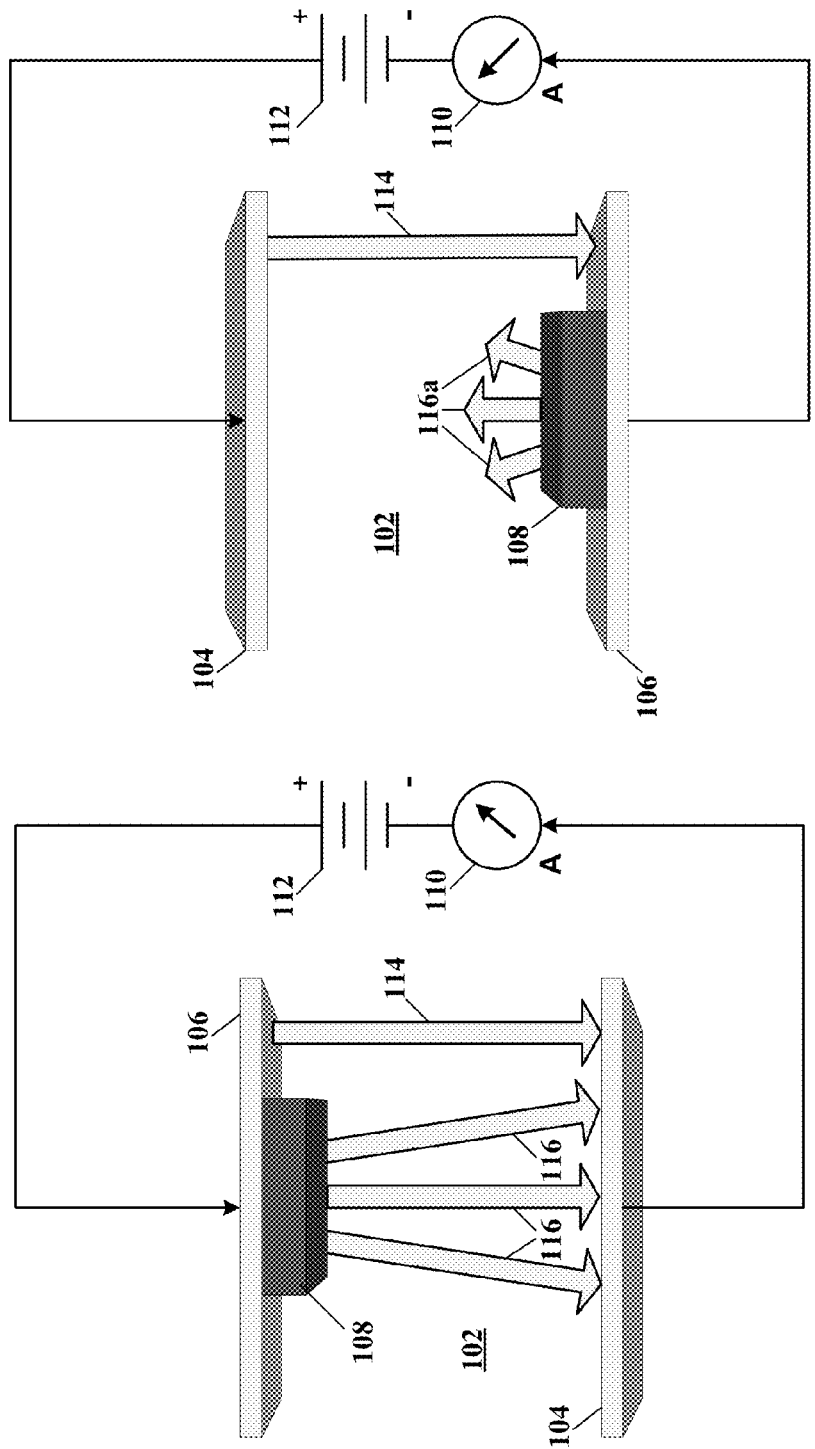
FIG. 1A illustrates schematic diagrams of an ion chamber having a radiation source and showing current flows therethrough for different polarity voltage source connections thereto.

Referring to FIG. 1A, depicted are schematic diagrams of an ion chamber having a radiation source and showing current flows therethrough for different polarity voltage source connections thereto. The ion chamber 102 may be characterized as three electrodes, e.g., electrodes 104, 106 and 210, having some ionized gas (e.g., air) molecules therebetween. The gas molecules are ionized by a radiation source 108. When a voltage potential 112 is applied between the two electrodes 104 and 106 at a first polarity (positive to electrode 106 and negative to electrode 104), a positively biased ionization electron current 116, $I_{chamber}$, will flow through the ionized gas. When the voltage potential 112 is applied between the two electrodes 104 and 106 at a second polarity (positive to electrode 104 and negative to electrode 106), substantially no negatively biased ionization electron current 116a will flow through the ionized gas since now the electrode 104 will repel the ionized gas electrons. However, leakage current 114, $I_{leakage}$, e.g., printed circuit board contaminates, grease, dust, etc., will flow irrespective of the connected polarity of the voltage potential 112.

Thus when the voltage potential 112 is connected at the first polarity across chamber 102 electrodes 104 and 106, the total current flow through the current meter 110 is the ionized electron current 116, $I_{chamber}$, plus the leakage current 114, $I_{leakage}$. And when the voltage potential 112 is connected at the second polarity across chamber 102 electrodes 104 and 106, the total current flow through the current meter 110 is substantially no ionized electron current 116a plus the leakage current 114, $I_{leakage}$, which results in substantially only the leakage current 114, $I_{leakage}$. Therefore, by subtracting the leakage current 114, $I_{leakage}$, from the total current flow, the actual ionized electron current 116, $I_{chamber}$, may be determined. This allows more sensitive measurements of any change in the ionized electron current 116, $I_{chamber}$, without these changes being masked by the undesired leakage current 114, $I_{leakage}$. It is contemplated and within the scope of this disclosure that any fluid, e.g., gas or liquid, that can be ionized by the ion source 108 will function as described hereinabove.

Figure 2:
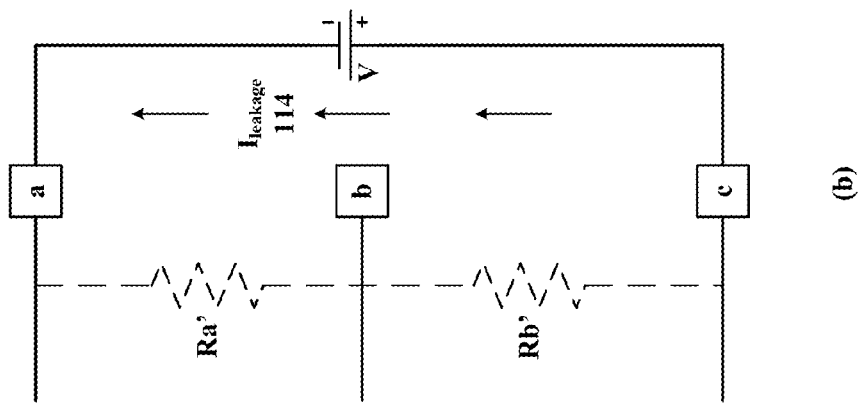
FIG. 2 illustrates a schematic elevational view of a typical two chamber smoke detection sensor having a radiation source.
Figure 2:
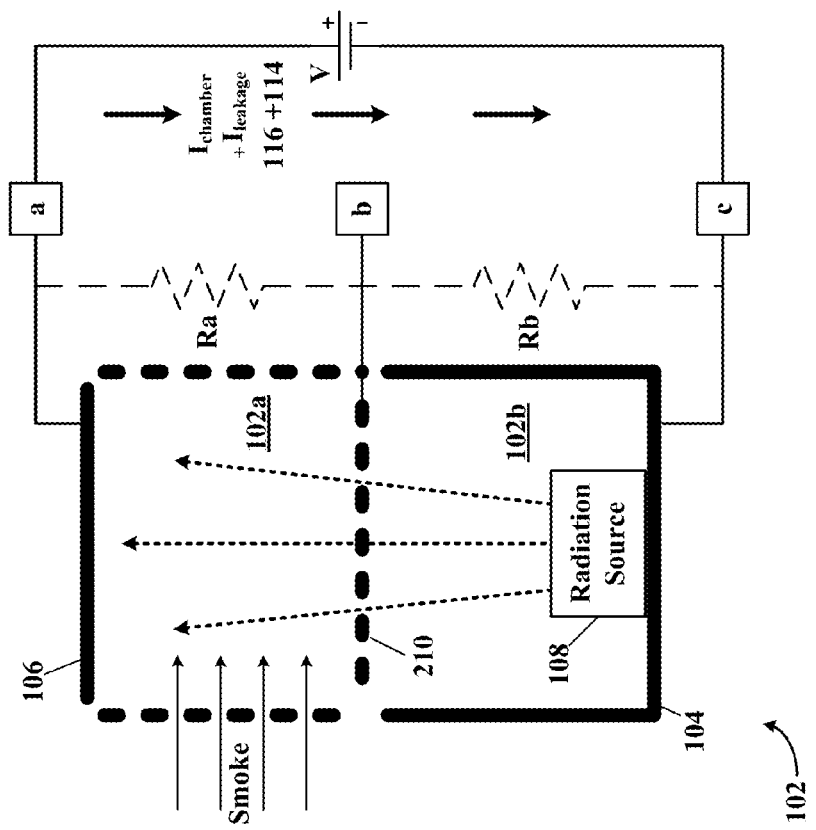

Referring to FIG. 2, depicted is a schematic elevational view of a typical two chamber smoke detection sensor having a radiation source. The ion chamber 102 is comprised of two chambers 102a and 102b. The top chamber 102a is open to ingress of smoke therein, and the bottom chamber 102b is closed to smoke ingress. A conductive screen 210 is located between the two chambers 102a and 102b. The radiation source 210 proximate to or in the ion chamber 102 causes some of the gas in the chambers 102a and 102b to ionize. This ionization of the gas causes an ionization current 116, $I_{chamber}$, to increase between the two electrodes 104 and 106 of the ion chamber 102.

When smoke is present in the top chamber 102a, it combines with the ionized gas, neutralizing some of the ionized gas from the current path of the ionization current 116, $I_{chamber}$. As a result, when smoke is present, the permittivity of the top chamber 102a is smaller than it would be in the lower chamber 102b. But since the ionized gases of the two chambers 102a and 102b are located in series with the current flowing between the electrodes 104 and 106, the ionization current 116, $I_{chamber}$, will be reduced. Since the conductive screen 210 is electrically floating, the top chamber 102a may be represented by a first resistance, Ra, and the bottom chamber 102b may be represented by a second resistance, Rb. When there is substantially the same number of ionized gas molecules in each of the two chambers 102a and 102b, the first resistance, Ra, will be substantially the same value as the second resistance, Rb, and the voltage drop across each ion chamber will be substantially the same. When smoke is introduced into the first chamber 102a, the first resistance, Ra, will be greater than the second resistance, Rb. Since the leakage current 114, $I_{leakage}$, must always be the same through both chambers 102a and 102b, there will be a first voltage between the electrode 106 and the conductive screen 210, and a second voltage between the conductive screen 210 and the electrode 104 that will change as the permittivity of each of the chambers 102a and 102b varies, i.e., the ion chamber having the lower permittivity will have a high voltage across its respective electrode and the conductive screen 210. Sensitivity in detecting changes between the first and second voltages may be reduced by the leakage current 114, $I_{leakage}$, since the desired current change is the change in the ionization electron current 116, $I_{chamber}$. In the configuration of (b) by comparing the voltage at terminal [b] when only the leakage current 114, $I_{leakage}$, is present from the configuration of (a) voltage at terminal [b] when both the ionized electron current 116, $I_{chamber}$, and the leakage current 114, $I_{leakage}$, are present. For example:

$$Vb=(Rb/(Ra+Rb))*(I_{chamber}+I_{leakage})$$

$$Vb=(Rb/(Ra+Rb))*(I_{chamber})+(Rb/(Ra+Rb))*(I_{leakage})$$

$$Vb'=(Rb'/(Ra'+Rb'))*(I_{leakage})$$

$$Vb_{chamber}=Vb-Vb'=(Rb/(Ra+Rb))*(I_{chamber})$$

Figure 3:
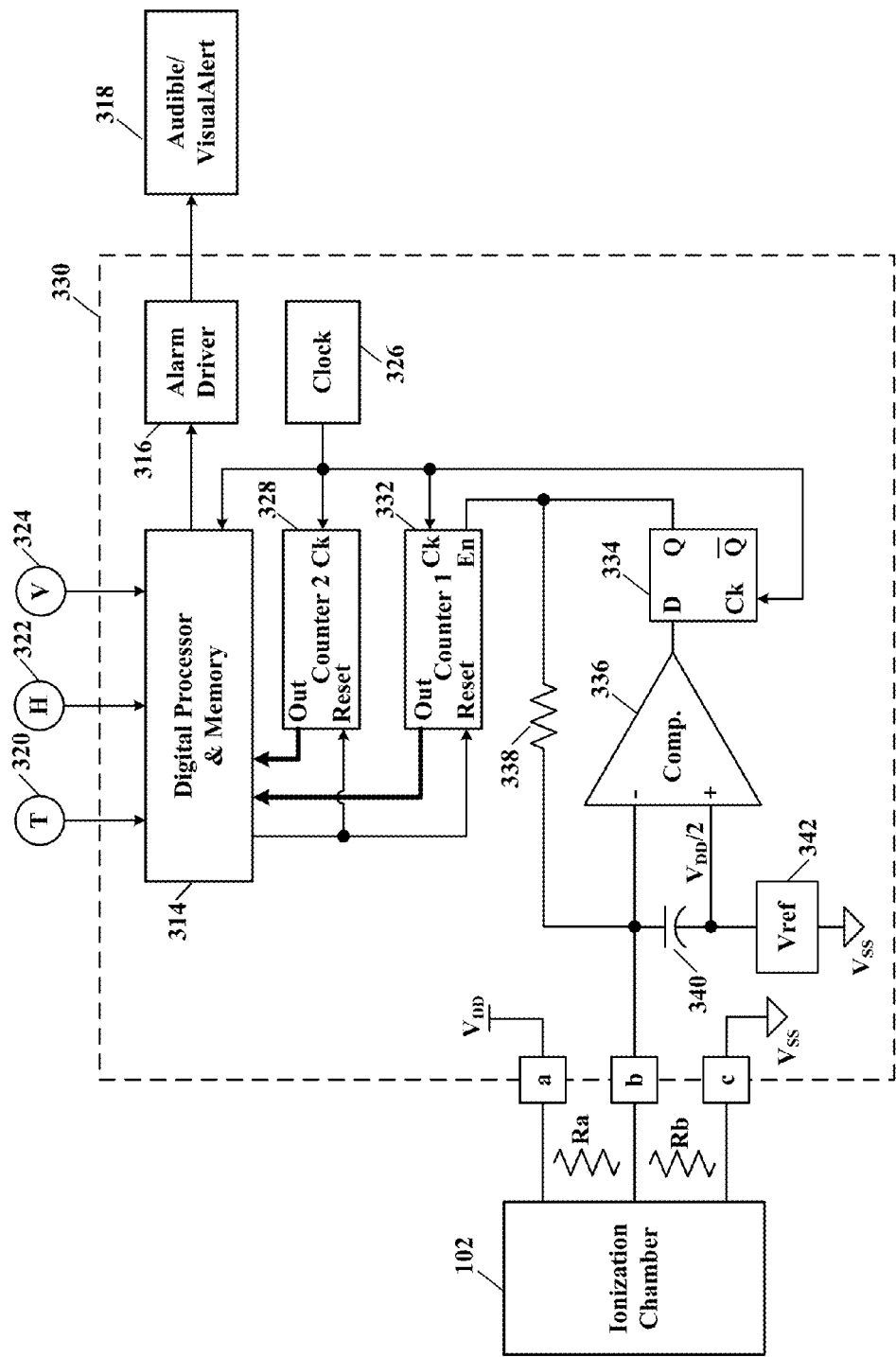
FIG. 3 illustrates a schematic block diagram of a smoke detector using a differential delta-sigma analog-to-digital converter (ADC), according to a specific example embodiment of this disclosure.

Referring to FIG. 3, depicted is a schematic block diagram of a smoke detector using a differential delta-sigma analog-to-digital converter (ADC), according to a specific example embodiment of this disclosure. A smoke detector, generally represented by the numeral 300, may comprise a smoke detection sensor ionization chamber 102, a digital processor and memory 314, an alarm driver 316, an audible/visual alert 318, a clock generator 326, a first counter 332, a second counter 328, a voltage comparator 336, a D flip-flop 334, a feedback resistor 338, an internal capacitor 340, and a voltage reference 342. All of the aforementioned elements except for the ionization chamber 102 and the audible/visual alert 318 may be provided in an integrated circuit microcontroller 330. When the digital processor 314 determines that there is smoke present, the alarm driver 316 will actuate the audible/visual alert 318.

The ion chamber 102 electrodes 106 and 104 may be coupled to a power supply $V_{DD}$ and the power supply common (e.g., $V_{SS}$) or any other voltage source that will cause a leakage current to flow between the two electrodes 106 and 104 (see FIG. 2). When the permittivity of each chamber 102a and 102b are the same, the voltage at the conductive screen 210 terminal [b] will be approximately $V_{DD}/2$. When the permittivity of the upper chamber 102a is reduced because of the presence of smoke therein, the voltage at the conductive screen 210 terminal [b] will be less than $V_{DD}/2$.

The comparator 336 has high impedance differential inputs and a low impedance output providing logic low "0" and logic high "1" levels. The positive input of the comparator 336 is coupled to a voltage reference 342 that provides a reference voltage of approximately $V_{DD}/2$. Other reference voltages may be provided by the voltage reference 342 and are contemplated herein for all purposes. The capacitor 340 is coupled between the negative and positive inputs of the comparator 336 and will charge to the voltage difference between the reference voltage of approximately $V_{DD}/2$ and the voltage at the conductive screen 210 terminal [b]. When the voltage at the negative input of comparator 336 is greater than (or equal to) the voltage at the positive input of comparator 336 the output thereof will be at a logic "0", e.g., substantially VSS. When the voltage at the negative input of comparator 336 is less than the voltage at the positive input of comparator 336 the output thereof will be at a logic "1", e.g., substantially $V_{DD}$.

The output of the comparator 336 is coupled to the D-input of the flip-flop 334 and every time a clock signal from the clock 326 is received at the clock input of the flip-flop 334 the logic level at the D-input will transfer to the Q-output of the flip-flop 334, e.g., substantially VDD or VSS. The feedback resistor 338 is coupled between the Q-output of the flip-flop 334 and the negative input of comparator 336 which is also coupled to the top of the capacitor 340. When the Q-output of the flip-flop 334 is at a logic "1" the capacitor 340 will charge to a higher voltage, and when Q-output of the flip-flop 334 is at a logic "0" the capacitor 340 will discharge to a lower voltage. Quiescent equilibrium will be reached when the negative and positive inputs of the comparator are at substantially the same voltages. For quiescent equilibrium during no smoke detection, with the voltage reference 342 at substantially $V_{DD}/2$, the logic 1/0 outputs of the flip-flop 334 will be at substantially a 50 percent duty cycle. If the voltage reference 342 output is less than $V_{DD}/2$, then the quiescent duty cycle will be less than 50 percent, and if the voltage reference 342 output is greater than $V_{DD}/2$, then the quiescent duty cycle will be greater than 50 percent. During quiescent conditions in the ion chamber 102, e.g., no smoke present in the upper chamber 102a, the conductive screen 210 terminal [b] will be at substantially $V_{DD}/2$. Smoke in the upper chamber 102a will cause the voltage at the conductive screen 210 terminal [b] to be less than $V_{DD}/2$ and the output of the comparator 336 be at a logic "1" ($V_{DD}$) more often than at a logic "0" until the negative and positive inputs of the comparator are at substantially the same voltages again. The comparator 336, flip-flop 334, feedback resistor 338 and capacitor 340 form a sigma-delta modulator.

The clock inputs of the first and second counters 332 and 328 are coupled to the clock generator 326 and increment each time a clock signal is received, except for the first counter 332 which will only increment when enabled. The enable input of the first counter 332 is coupled to the Q-output of the flip-flop 334 and its count is thereby controlled to count only when the Q-output is at one or the other logic level, e.g., at a logic "1". The maximum count values of the first and second counters 332 and 328 may be as large as necessary, e.g., 16 bits. The first and second counters 332 and 328 may also be concatenated, e.g., a plurality of first and second counters 332 and 328. The larger the count value, the greater the resolution but also an increase in the time required for analog-to-digital conversion. By applying an appropriate clock speed, and appropriate values for the feedback resistor 338 and capacitor 340, very high resolution may be obtained that will allow the digital processor to easily discern when there is a smoke detection event in the smoke detection ionization chamber 102.

Since the first counter 332 will only count when the Q-output of the flip-flop 334 is at one of the logics, e.g., logic "1" for the following explanation, for a reference voltage at approximately $V_{DD}/2$ and no smoke in the upper chamber 102a the count value will be approximately half the count value of the second counter 328 which counts continuously. When there is smoke present in the upper chamber 102a and the voltage at the conductive screen 210 terminal [b] is less than $V_{DD}/2$, the Q-output of the flip-flop 334 will be at a logic "0" more often than at a logic "1". Therefore, the count value of the first counter 332 will be less than half of the count value of the second counter 328, e.g., more zeros "0s" than "1s".

The digital processor 314 reads the first and second count values of the first and second counters 332 and 328, respectively, then resets them to begin counting again. From the read first and second count values the digital processor 314 can determine when a smoke event has occurred. The digital processor may also do decimation of these count values, averaging, etc. For example, the first count value is subtracted from the second count value to produce a difference value for the top chamber 102a and the bottom chamber 102b. The value for the top chamber 102a is then divided by the value for the bottom chamber 102b to produce an output value. By dividing the two chamber values by one another, any shift due to battery voltage or temperature change is removed and the remaining value is a proportional value of the relative leakage of the two chambers 102a and 102b.

The smoke detector 300 may further comprise a temperature sensor 320, a relative humidity sensor 322, and/or a voltage sensor 324 coupled to a power supply, e.g., battery (not shown). Wherein the digital processor 314 may compensate for leakage current measurements that may change under different temperature, humidity and/or voltage conditions, e.g., using look-up tables that contain calibration and compensation data for the smoke sensor ion chamber 102. In addition, the digital processor 314 may perform smoothing, time averaging, noise suppression, over sampling, decimation, and/or digital signal processing to enhance the leakage current change detection sensitivity and/or reduce noise pick-up.

Figure 4:
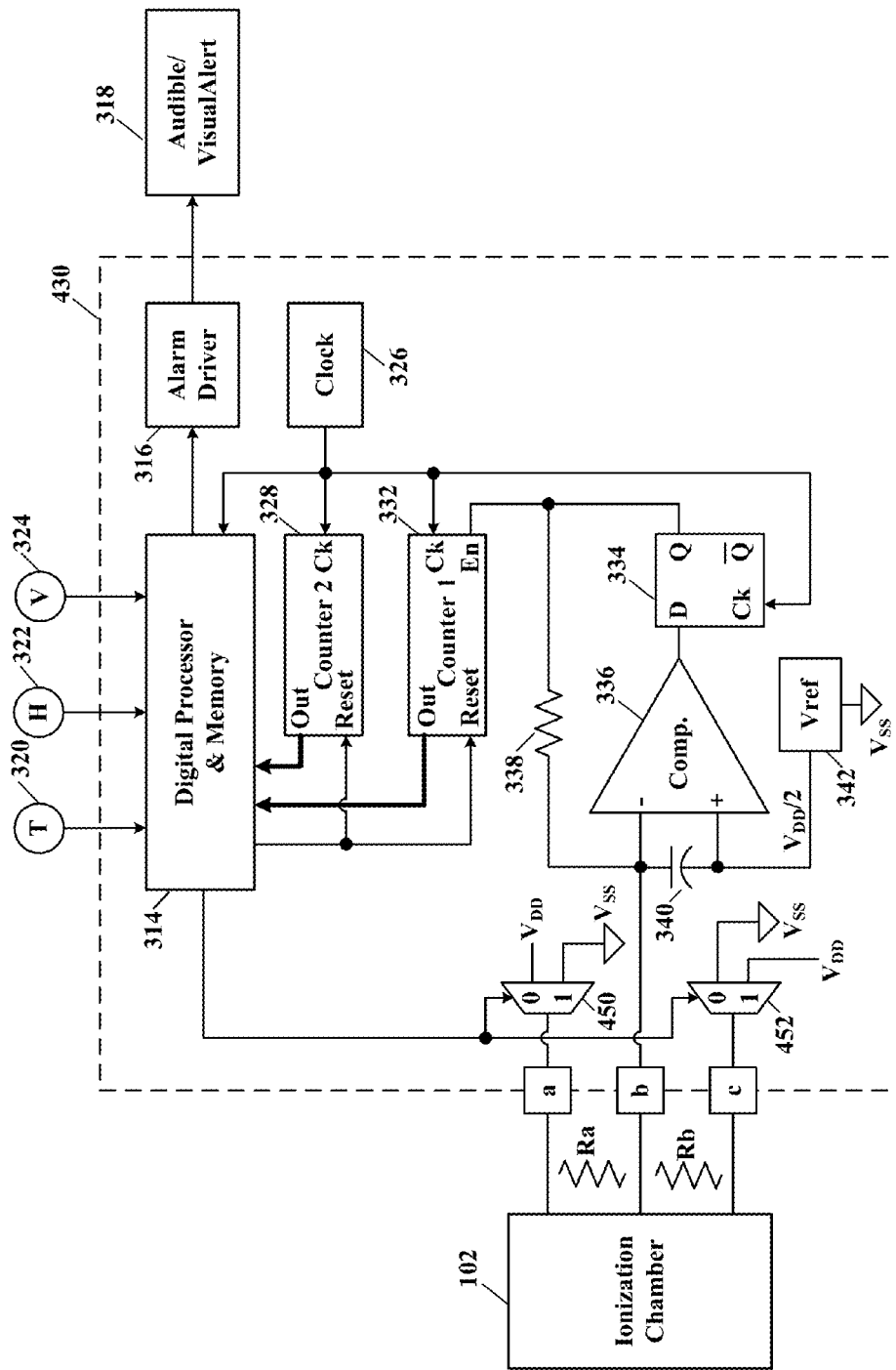
FIG. 4 illustrates a schematic block diagram of a smoke detector using a differential delta-sigma analog-to-digital converter (ADC) and having rejection of common mode leakage current, according to another specific example embodiment of this disclosure.

Referring to FIG. 4, depicted a schematic block diagram of a smoke detector using a differential delta-sigma analog-to-digital converter (ADC) and having rejection of common mode leakage current, according to another specific example embodiment of this disclosure. A smoke detector, generally represented by the numeral 400, measures the voltage at the conductive screen 210 terminal [b] in substantially the same way as the smoke detector 300 described hereinabove. A further refinement to the operation of the smoke detector 400 is the removal of the common mode leakage current 114 that reduces the smoke detection sensitivity of the ionization chamber 102. The smoke detector 400 further comprises multiplexers 450 and 452 that reverse the voltage polarity on the ionization chamber 102 (see FIG. 1A). The digital processor 314 controls the multiplexers 450 and 452, when a first voltage at the conductive screen 210 terminal [b] is measured at a chamber first polarity, and a second voltage at the conductive screen 210 terminal [b] is measured at a chamber second polarity, wherein the chamber second polarity is opposite the chamber first polarity. These voltage measurements are stored in the memory of the digital processor 314 for further processing to enhance the voltage change sensitivity and thereby increased the detection sensitivity of the smoke detector 400.

Also a further enhancement to more reliable smoke detection is to require that the change in leakage current occurs in less than or equal to a certain time period so as to reject slow leakage current change due to changes in temperature, relative humidity and/or supply voltage (e.g., battery not shown).

It is contemplated and within the scope of this disclosure that the digital processor and memory 314 may go into a low power sleep mode while the first and second counters 332 and 328 are counting, and only wake up to read the count values therefrom and do appropriate calculations in determining whether there is smoke in the first chamber 102a. All other functions and circuits described hereinabove remain in an active mode but are all very low power. Also the second counter 328 may be a wake-up timer inherent with a low power, standby sleep mode function in a microcontroller. This sleep mode further increase battery life of the smoke detector 300.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A method for detecting smoke, comprising the steps of:
   determining a voltage on a conductive screen with a delta-sigma analog-to-digital converter, wherein the conductive screen is located between a first ion chamber and a second ion chamber, wherein the first ion chamber is open to smoke ingress and the second ion chamber is closed to smoke ingress; and
   detecting a presence of smoke by:
   applying a first voltage potential to the first and second ion chambers at a first polarity;
   determining a first voltage on the conductive screen caused by the first voltage potential at the first polarity;
   applying a second voltage potential to the first and second ion chambers at a second polarity;
   determining a second voltage on the conductive screen caused by the second voltage potential at the second polarity;
   determining a voltage difference between the first and the second voltages; and
   detecting the presence of smoke when the voltage difference changes by a certain amount.

2. The method according to claim 1, wherein the steps of applying the first or applying the second voltage are performed using first and second multiplexers.

3. The method according to claim 1, wherein the presence of smoke is detected if the voltage on the conductive screen changes by the certain amount within a certain time.

4. The method according to claim 1, where the step of determining the first voltage and the step of determining the second voltage each comprise:
   comparing the voltage on the conductive screen to a reference voltage from a voltage reference with a voltage comparator;
   charging a capacitance coupled between the conductive screen and the voltage reference when the voltage on the conductive screen is less than the reference voltage;
   discharging the capacitance coupled between the conductive screen and the voltage reference when the voltage on the conductive screen is greater than the reference voltage;
   generating a pulse width modulated signal with respect to charging and discharging of the capacitance; and
   determining a duty cycle of the pulse width modulated signal.

5. The method according to claim 4, wherein the duty cycle of the pulse width modulated signal is determined by clocked timers.

6. The method according to claim 1, further comprising the step of compensating for temperature change with temperature information from a temperature sensor.

7. The method according to claim 1, further comprising the step of compensating for relative humidity change with relative humidity information from a relative humidity sensor.

8. The method according to claim 1, further comprising the step of compensating for voltage change with voltage information from a voltage sensor.

9. The method according to claim 4, wherein the analog-to-digital digital converter is part of a microcontroller and controlled by a digital processor of the microcontroller, wherein the digital processor goes into a low power sleep mode when the cloked timers are counting.

10. The method according to claim 9, further comprising waking up the digital processor to read count values of the clocked timers.

11. An apparatus for detecting smoke, comprising:
an ionization chamber having a radiation source and comprising first and second chambers with a conductive screen there between, wherein the first chamber is open to smoke ingress and the second chamber is closed to smoke ingress;
a voltage comparator having a first input coupled to the conductive screen and a second input coupled to a voltage reference;
a capacitor coupled between the first and second inputs of the voltage comparator;
a flip-flop having a D-input coupled to an output of the voltage comparator and a clock input coupled to a clock generator, wherein each time a clock signal is received from the clock generator a logic value at the D-input is transferred to a Q-output of the flip-flop;
a feedback resistor coupled between the Q-output of the flip-flop and the first input of the voltage comparator for charging and discharging the capacitor;
wherein when a voltage on the first input of the voltage comparator is greater than a voltage from the voltage reference the output of the voltage comparator is at a logic low and the capacitor is discharged, and when the voltage on the first input of the voltage comparator is less than the voltage from the voltage reference the output of the voltage comparator is at a logic high and the capacitor is charged;
a first counter for counting a first number of clock pulses from the clock generator when the Q-output of the flip-flop is at a logic high during a certain time period; and
a second counter for counting a second number of clock pulses from the clock generator during a certain time period;
wherein when the first number changes a certain amount within the certain time period a presence of smoke is detected within the first chamber.

12. The apparatus for detecting smoke according to claim 11, further comprising circuits for alternately coupling the ionization chamber to voltage potentials at first or second polarities, wherein the second polarity is opposite the first polarity.

13. The apparatus for detecting smoke according to claim 12, wherein the circuits for alternately coupling comprises voltage multiplexers.

14. The apparatus for detecting smoke according to claim 11, wherein the ionization chamber is coupled to a microcontroller having a digital processor and memory, and the microcontroller performs all of the aforementioned functions for detecting the presence of smoke.

15. The apparatus for detecting smoke according to claim 14, further comprising an alarm circuit coupled to the digital processor.

16. The apparatus for detecting smoke according to claim 14, further comprising a temperature sensor coupled to the digital processor and a temperature compensation look-up table stored in the memory coupled to the digital processor and used to compensate temperature induced changes of the capacitance of the ionization chamber.

17. The apparatus for detecting smoke according to claim 14, further comprising a humidity sensor coupled to the digital processor and a humidity compensation look-up table stored in the memory coupled to the digital processor and used to compensate humidity induced changes of the capacitance of the ionization chamber.

18. The apparatus for detecting smoke according to claim 14, further comprising a voltage sensor coupled to the digital processor and a voltage compensation look-up table stored in the memory coupled to the digital processor and used to compensate voltage induced changes of the capacitance of the ionization chamber.

19. The apparatus for detecting smoke according to claim 11, further comprising an audible alert actuated by the presence of smoke in the ionization chamber.

20. The apparatus for detecting smoke according to claim 11, further comprising a visual alert actuated by the presence of smoke in the ionization chamber.

21. The apparatus for detecting smoke according to claim 14, further comprising a microcontroller having a low power sleep mode, wherein the digital processor and memory of the microcontroller go into the low power sleep mode during counting by the first and second counters.

22. The apparatus for detecting smoke according to claim 21, wherein the second counter is a sleep wake-up timer for the digital processor and memory of the microcontroller.

23. An apparatus for detecting smoke, comprising:
an ionization chamber having a radiation source and comprising first and second chambers with a conductive screen there between, wherein the first chamber is open to smoke ingress and the second chamber is closed to smoke ingress;
an analog-to-digital converter (ADC) coupled with the conductive screen;
circuits for alternately coupling the ionization chamber to voltage potentials at first or second polarities, wherein the second polarity is opposite the first polarity;
wherein the apparatus is configured to control the circuits for alternately coupling the ionization chamber to voltage potentials to apply a voltage potential having the first polarity to said ionization chamber and measure a first voltage with said ADC and subsequently to apply a voltage potential having the second polarity to said ionization chamber and measure a second voltage with said ADC,
wherein the apparatus is further configured to determine a voltage difference between the first and the second voltages and to detect the presence of smoke when the voltage difference changes by a certain amount.

24. The apparatus for detecting smoke according to claim 23, wherein the analog-to-digital converter comprises:
a voltage comparator having a first input coupled to the conductive screen and a second input coupled to a voltage reference;
a capacitor coupled between the first and second inputs of the voltage comparator;
a flip-flop having a D-input coupled to an output of the voltage comparator and a clock input coupled to a clock generator, wherein each time a clock signal is received from the clock generator a logic value at the D-input is transferred to a Q-output of the flip-flop;

a feedback resistor coupled between the Q-output of the flip-flop and the first input of the voltage comparator for charging and discharging the capacitor;

wherein when a voltage on the first input of the voltage comparator is greater than a voltage from the voltage reference the output of the voltage comparator is at a logic low and the capacitor is discharged, and when the voltage on the first input of the voltage comparator is less than the voltage from the voltage reference the output of the voltage comparator is at a logic high and the capacitor is charged;

a first counter for counting a first number of clock pulses from the clock generator when the Q-output of the flip-flop is at a logic high during a certain time period; and a second counter for counting a second number of clock pulses from the clock generator during a certain time period.

25. The apparatus for detecting smoke according to claim 23, wherein the analog-to-digital converter and circuits for alternately coupling the ionization chamber to voltage potentials are part of a microcontroller comprising a digital processor, and wherein the second counter is formed by a wake-up timer of the microcontroller.

26. The apparatus for detecting smoke according to claim 23, further comprising an alarm circuit coupled to a digital processor configured to generate an audible alert actuated by the presence of smoke in the ionization chamber.

27. The apparatus for detecting smoke according to claim 23, further comprising a temperature sensor coupled to a digital processor and a temperature compensation look-up table stored in a memory coupled to the digital processor and used to compensate temperature induced changes of a capacitance of the ionization chamber.

28. The apparatus for detecting smoke according to claim 23, further comprising
a humidity sensor coupled to a digital processor and a humidity compensation look-up table stored in the memory coupled to the digital processor and used to compensate humidity induced changes of the capacitance of the ionization chamber.

29. The apparatus for detecting smoke according to claim 23, further comprising
a voltage sensor coupled to a digital processor and a voltage compensation look-up table stored in the memory coupled to the digital processor and used to compensate voltage induced changes of the capacitance of the ionization chamber.

30. The apparatus for detecting smoke according to claim 23, further comprising an alarm circuit coupled to a digital processor configured to generate a visual alert actuated by the presence of smoke in the ionization chamber.

31. The apparatus for detecting smoke according to claim 24, further comprising a microcontroller comprising a digital processor and memory having a low power sleep mode, the circuits for alternately coupling the ionization chamber to voltage potentials, and said ADC, wherein the digital processor and memory of the microcontroller go into the low power sleep mode during counting by the first and second counters.

32. The apparatus for detecting smoke according to claim 31, wherein the second counter is a sleep wake-up timer for the digital processor and memory of the microcontroller.

* * * * *

UNITED STATES PATENT AND TRADEMARK OFFICE
CERTIFICATE OF CORRECTION

| | | |
|---|---|---|
| PATENT NO. | : 9,207,209 B2 | Page 1 of 1 |
| APPLICATION NO. | : 13/667165 | |
| DATED | : December 8, 2015 | |
| INVENTOR(S) | : Cooke et al. | |

It is certified that error appears in the above-identified patent and that said Letters Patent is hereby corrected as shown below:

Column 11,
Claim 9, line 8, "…to-digital digital converter is part of a microcontroller and…" ---Change to---
"…to-digital converter is part of a microcontroller and…"

Column 11,
Claim 9, line 12, "…mode when the cloked timers are counting…" ---Change to---
"…mode when the clocked timers are counting…"

Signed and Sealed this
Twenty-ninth Day of March, 2016

Michelle K. Lee
*Director of the United States Patent and Trademark Office*